(12) United States Patent
Hashiguchi et al.

(10) Patent No.: US 6,547,727 B1
(45) Date of Patent: Apr. 15, 2003

(54) METHOD OF SUPPORTING HEALTH CHECKUP, AN APPARATUS FOR IMPLEMENTING THE SAME AND A MEDIUM RECORDING THEIR PROCESSING PROGRAMS

(75) Inventors: Takeshi Hashiguchi, Tokyo-to (JP); Hiroshi Takeuchi, Matsudo (JP); Hitoshi Matsuo, Musashino (JP); Kiyoteru Noguchi, Tokyo-to (JP); Kazuyuki Shimada, Kawaguchi (JP)

(73) Assignee: Hitachi, Ltd., Tokyo (JP)

( * ) Notice: Subject to any disclaimer, the term of this patent is extended or adjusted under 35 U.S.C. 154(b) by 0 days.

(21) Appl. No.: 09/493,078

(22) Filed: Jan. 28, 2000

(30) Foreign Application Priority Data

Mar. 17, 1999 (JP) .......................................... 11-071332

(51) Int. Cl.$^7$ .......................... A61B 5/00; A61B 10/00; G06F 17/60; G06K 9/62
(52) U.S. Cl. .......................... 600/300; 705/3; 128/920; 128/923
(58) Field of Search .............................. 600/300–301, 600/309, 345–347, 365; 128/904, 920–925; 705/2–3, 9; 706/16, 21–22, 25

(56) References Cited

U.S. PATENT DOCUMENTS

| | | | | |
|---|---|---|---|---|
| 5,935,060 A | * | 8/1999 | Iliff | 600/300 |
| 6,246,975 B1 | * | 6/2001 | Rivonelli et al. | 703/11 |
| 6,248,063 B1 | * | 6/2001 | Barnhill et al. | 600/300 |
| 6,269,339 B1 | * | 7/2001 | Silver | 705/2 |

* cited by examiner

Primary Examiner—Max F. Hindenburg
Assistant Examiner—Michael Astorino
(74) Attorney, Agent, or Firm—Antonelli, Terry, Stout & Kraus, LLP

(57) ABSTRACT

In a health checkup supporting method for predicting a health checkup receiver's risk of suffering from a disease, steps are provided to input checkup receiver information indicating the possibilities of a disease being contracted by a checkup receiver and to obtain a risk value indicating a degree of the checkup receiver's possible incidence of the disease based on inputted checkup receiver information and a risk parameter obtained from the ratio of past disease patients.

16 Claims, 9 Drawing Sheets

FIG.3

| Checkup Receiver ID | Date of Data Entry | Results of Clinical Examination | | | Results of Question-and-Answer Examination | | | | Results of Genetic Examination | | | |
|---|---|---|---|---|---|---|---|---|---|---|---|---|
| | | Fasting Blood Glucose Value | Glucose Tolerance Test | Glycuresis | ... | Q1 | Q2 | Q3 | ... | NIDDM1 | NIDDM2 | NIDDM3 | ... |
| 106 | 99/02/26 | 1 | 2 | 4 | | ○ | | ○ | | ○ | | | |

Interview sheet

Q1. Do you have your skin itching?

Q2. Are you liable to have botching and not quick to have it recovered?

Q3. Do you feel that your eyesight is weakening?
(Do you need to wear glasses or do you need to get glasses adjusted?)

Q4. Not neuralgia nor rheumatic, do you tend to have your legs aching and free from it after a short rest?

| Items to Be Checked at Clinical Examination for Diabetes | | | | Risk Parameter p1 |
|---|---|---|---|---|
| Fasting Blood Glucose Value | Glucose Tolerance Test | Glycuresis | ... | |
| 1 | 1 | 1 | | 0.20 |
| 1 | 1 | 2 | | 0.23 |
| 1 | 1 | 3 | | 0.25 |
| 1 | 1 | 4 | | 0.30 |
| 1 | 2 | 1 | | 0.21 |
| 1 | 2 | 2 | | 0.24 |
| 1 | 2 | 3 | | 0.27 |
| 1 | 2 | 4 | | 0.31 |

| Question-and-Answer Items for Diabetes | | | | Risk Parameter p2 |
|---|---|---|---|---|
| Q1 | Q2 | Q3 | ... | |
|  |  |  |  | 0.20 |
|  | O |  |  | 0.23 |
|  |  | O |  | 0.25 |
|  | O | O |  | 0.30 |
| O |  |  |  | 0.21 |
| O | O |  |  | 0.24 |
| O |  | O |  | 0.27 |
| O | O | O |  | 0.31 |

FIG.8

| Checkup Receiver ID | Date of Data Entry | Results of Clinical Examination ||| | Results of Question-and-Answer Examination |||| | Results of Genetic Examination |||| | History of Diseases |
|---|---|---|---|---|---|---|---|---|---|---|---|---|---|---|
| | | Fasting Blood Glucose Value | Glucose Tolerance Test | Glycuresis | ... | Q1 | Q2 | Q3 | ... | NIDDM1 | NIDDM2 | NIDDM3 | ... | |
| 101 | 99/02/16 | 1 | 1 | 1 | | | | | | | | | | |
| 102 | 99/02/17 | 1 | 2 | 4 | | ○ | | | | | | | | Incidence of Diabetes |
| 103 | 99/02/19 | 1 | 1 | 2 | | ○ | | ○ | | ○ | | | | |
| 104 | 99/02/21 | 1 | 2 | 1 | | | | ○ | | | ○ | | | |
| 105 | 99/02/22 | 1 | 2 | 3 | | ○ | ○ | ○ | | | | | | |
| 106 | 99/02/26 | 1 | 2 | 4 | | ○ | | ○ | | ○ | | | | |
| .. | | | | | | | | | | | | | | |

METHOD OF SUPPORTING HEALTH CHECKUP, AN APPARATUS FOR IMPLEMENTING THE SAME AND A MEDIUM RECORDING THEIR PROCESSING PROGRAMS

BACKGROUND OF THE INVENTION

The present invention relates to a health checkup system which operates to diagnose the health status of a checkup receiver; and, more particularly, the invention relates to a technique which is applicable to a health checkup system to predict the risk of a checkup receiver suffering from a disease based on the combined results of a clinical examination, a question-and-answer examination and a genetic examination.

When a person wishes to know the status of his health or to predict how much risk he or she has of suffering a certain disease he or she may possibly be exposed to while leading a certain life-style, it is general to obtain a health checkup.

In a conventional health checkup, the health status of a health checkup receiver is examined through a clinical examination and a question-and-answer examination, and the health status of the health checkup receiver is diagnosed on the basis of the results of these examinations compared with the average results obtained from healthy persons. Receiving such a health checkup, a person can roughly know the possibility of developing a certain disease and utilize this result as a guidance to improve his daily life style.

In recent years, meanwhile, there has been increased use of a genetic examination for detecting gene mutation in a sample, such as blood. A medical examination of this kind is only applicable to diseases for which the genes which cause the disease have been determined. Despite this, the above-described examination is advantageous in that it makes a precritical diagnosis possible. Therefore, this examination is often conducted as a prenatal checkup to diagnose gene-caused diseases with the mutation of specific genes being known as their causes.

Incidentally, a system of predicting the life-time incidence of Alzheimer's disease, which is capable of accurately obtaining data constituting a basis for the judgment of an early examination and treatment of Alzheimer's disease, is disclosed in Japanese Patent Laid-Open No. Hei 10-261029.

The above-described conventional health checkup to diagnose the health status of a checkup receiver by comparing the results of a clinical examination and a question-and-answer examination with average values makes it hard to conduct a diagnosis incorporating personal differences.

The above genetic examination is conducted with the checkup receiver's personal genetic difference taken into account. However, it is difficult to perform a diagnosis using only a genetic examination, since it is not applicable to diseases for which the genes which cause the disease are not determined or diseases depending on various genes and environmental factors.

SUMMARY OF THE INVENTION

In view of the above, the present invention has as its object to resolve the above problems and to provide a technique to enhance the precision of calculation of a value of a health checkup receiver's risk to a disease.

According to the present invention, a check receiver's risk of suffering from a disease is predicted based on a combination of the results of a clinical examination, the results of a question-and-answer examination and the results of a genetic examination in a health checkup system for predicting a risk of incidence of a disease of a checkup receiver who has received a health checkup.

According to the present invention, the results of a clinical examination indicating the bio-information of a checkup receiver, the results of a question-and-answer examination indicating information including the habitual activities of the checkup receiver and the results of a genetic examination indicating the genetic characteristics of the checkup receiver as an individual are inputted as checkup receiver information showing the possibilities of affecting the incidence of a disease obtained with respect to the checkup receiver who has received a health checkup.

By comparing the inputted checkup receiver information with risk parameters obtained from a disease incidence ratio calculated for other persons in the past, a risk value of the possible incidence of a disease is found and diagnostic messages and remedial measures are indicated in correspondence with the obtained risk value.

According to the present invention, as described above, since the results of a genetic examination showing the genetic characteristics of a checkup receiver are used for a diagnosis in addition to the results of a clinical examination indicating the bio-information of the checkup receiver and the results of the question-and-answer examination including the checkup receiver's habitual activities, it is possible to diagnose the checkup receiver's liability to contact a life-dependent disease based on a certain life-style and genetic characteristics, thereby providing a diagnosis which matches the characteristics of a health checkup receiver.

Since environmental factors such as life habits and the results of a genetic examination are diagnosed together, it is possible to diagnose a disease which cannot be diagnosed only through an examination of genes which are known to cause a disease, thereby widening the range of diseases it can diagnose.

As described above, the health checkup system according to the present invention conducts a risk prediction of a disease of a checkup receiver based on the results of a genetic examination indicating the genetic characteristics of an individual together with the results of a clinical examination and a question-and-answer examination, so that the precision of the calculation of a risk value with respect to a health checkup receiver can be enhanced.

BRIEF DESCRIPTION OF THE DRAWINGS

FIG. 3 is a table showing an example of checkup receiver information according to the present invention;

FIG. 4 is a diagram showing an example of a question-and-answer examination interview sheet according to the present invention;

FIG. 5 is a table showing an example of a clinical Examination result parameter table 107 according to the present invention;

FIG. 6 is a table showing an example of a question-and-answer examination result parameter table 108 according to the present invention;

FIG. 8 is a table showing an example of a checkup receiver information database 207 according to the present invention;

DETAILED DESCRIPTION OF PREFERRED EMBODIMENTS

Now, there will be explained a health checkup system embodying the present invention to predict a checkup receiver's risk of suffering from a disease.

Figure 1:
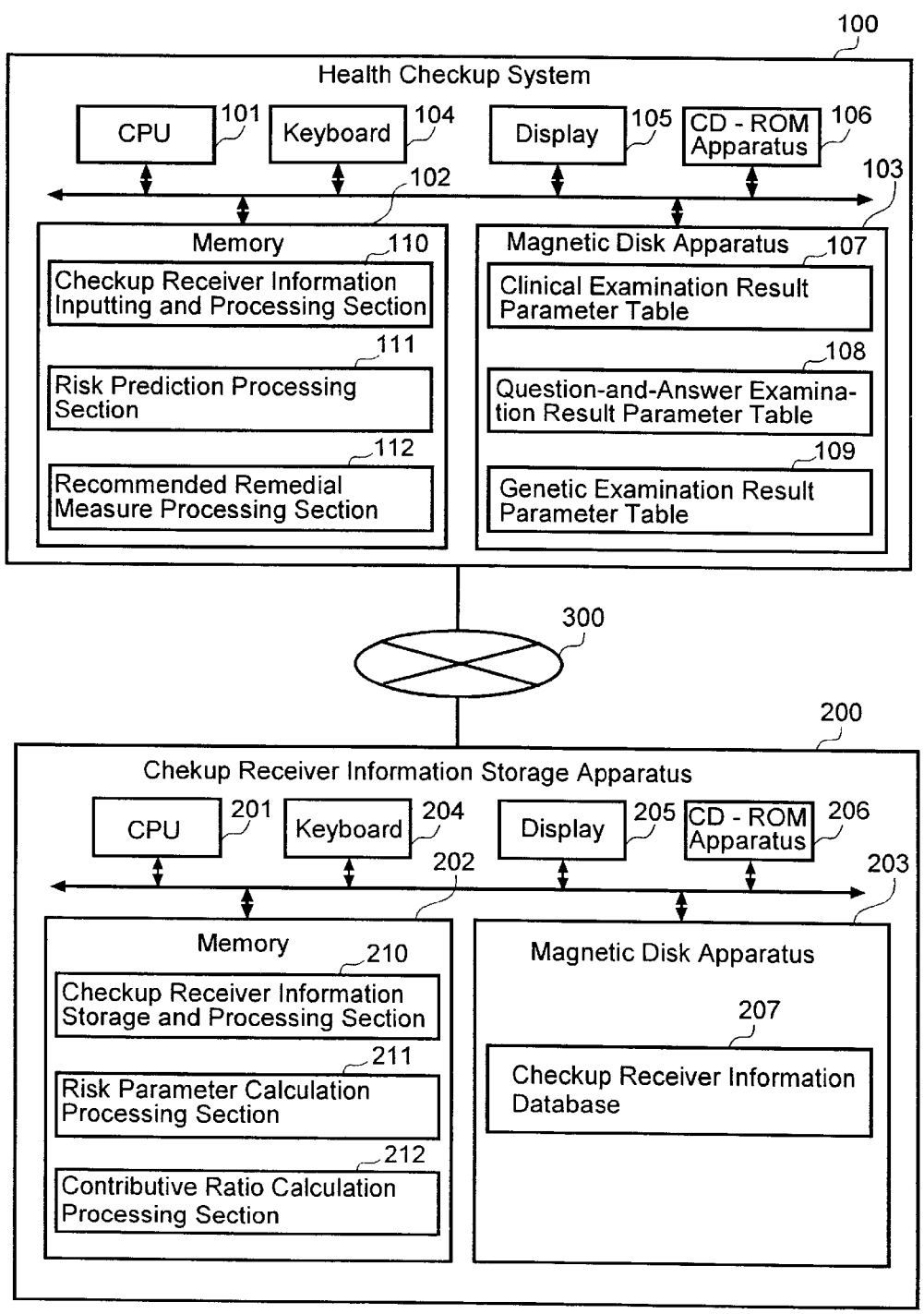
FIG. 1 is a diagram showing a schematic configuration of a health checkup system according to the present invention.

FIG. 1 is a diagram showing a schematic configuration of a health checkup system according to the present invention. As shown in FIG. 1, a health checkup apparatus 100, representing an embodiment according to the present invention, comprises CPU 101, a memory 102, a magnetic disk apparatus 103, a keyboard 104, a display 105, a CD-ROM apparatus 106, a clinical examination result parameter table 107, a question-and-answer result parameter table 108 and a genetic examination result parameter table 109.

CPU 101 is a control device to control the overall operation of the health check apparatus 100. The memory 102 is a memory device which loads various programs to control the health checkup system 100, as well as data. The magnetic disk apparatus 103 is a memory device to store the above processing programs and data.

The keyboard 104 is an input device to conduct input operations such as the designation of a disease with respect to which a risk value is to be calculated. The display 105 is an output device to display diagnostic messages, including the result of a risk value calculation, and remedial measures, among other things.

The CD-ROM apparatus 106 is a device to read a CD-ROM which stores the above-described processing programs and data. The clinical examination result parameter table 107 is a table storing risk parameters corresponding to the results of clinical examinations conducted in the past.

The question-and-answer examination result parameter table 108 is a table storing risk parameters corresponding to the results of question-and-answer examinations conducted in the past. The genetic examination result parameter table 109 is a table storing risk parameters corresponding to the results of genetic examinations conducted in the past.

The health checkup apparatus 100 has a checkup receiver information inputting and processing section 110, a risk prediction processing section 111 and a recommended remedial measure presenting and processing section 112.

The checkup receiver information inputting and processing section 110 is a processing section which operates to input checkup receiver information showing the disease-incidence risk of a checkup receiver who has received a health checkup. The risk prediction processing section 111 is a processing section which operates to calculate the risk value of the checkup receiver's risk of suffering from a disease based on the inputted checkup receiver information and risk parameters for the incidence of a disease obtained from health checkup receivers in the past. The recommended remedial measure presenting and processing section 112 is a processing section which operates to show a remedial measure to lower the above-described risk value if it is higher than a predetermined value.

A program to make the health checkup apparatus 100 function as the checkup receiver information inputting and processing section 110, the risk prediction processing section 111 and the remedial measure presenting and processing section 112 is first recorded on a medium such as a CD-ROM, from which it is loaded into the memory for its execution. A medium recording the program may be anything other than CD-ROM.

A checkup receiver information storage apparatus 200 is composed of CPU 201, a memory 202, a magnetic disk apparatus 203, a keyboard 204, a display 205, a CD-ROM apparatus 206 and a checkup receiver information database 207.

CPU 201 is a control apparatus which operates to control the overall operation of the checkup receiver information storage apparatus 200. The memory 202 is a memory apparatus to load various programs for controlling the operations of the checkup receiver information storage apparatus 200, as well as data.

The magnetic disk apparatus 203 is a memory apparatus to store the above processing programs and data. The keyboard 204 is an input apparatus to instruct and execute the calculation of risk parameters and their contributive ratios. The display 205 is an output apparatus which displays the results of processing of risk parameters and their contributive ratios.

The CD-ROM apparatus 206 is a device to read a CD-ROM which stores the processing programs and data described above. The checkup receiver information database 207 is a database to store information obtained from a health checkup receiver at the time of the health checkup and patient information obtained from outpatients visiting a hospital after the incidence of a disease.

The checkup receiver information storage apparatus 200 has a checkup receiver information storage and processing section 210, a risk parameter calculation processing section 211 and a contributive ratio calculation processing section 212.

The checkup receiver information storage and processing apparatus 210 is a processing section which operates to store in the checkup receiver information database 207 the checkup receiver information obtained at the time of a health checkup and information obtained from outpatients visiting a hospital after the incidence of a disease. The risk parameter calculation processing section 211 is a processing section which operates to calculate the risk parameters. The contributive ratio calculation processing section 212 is a processing section which operates to calculate the contributive ratio of each risk parameter in order to work out the above risk value.

A program to make the checkup receiver information storage apparatus 200 function as the checkup receiver information storage and processing apparatus 210, the risk parameter calculation processing section 211 and the contributive ratio calculation processing section 212 is first recorded on a medium such as a CD-ROM, from which it is loaded into the memory for its execution. The medium recording the program also may be a storage medium other than a CD-ROM.

As shown in FIG. 1, the health checkup apparatus 100 in this embodiment of the present invention is connected to the checkup receiver information storage apparatus 200 through a network 300, so that a checkup receiver information inputted into the health checkup apparatus 100 is fed to the checkup receiver information storage apparatus 200 through the network 300. In this embodiment of the present invention, only the single health checkup apparatus 100 is connected to the checkup receiver information storage apparatus 200. However, the checkup receiver information storage system 200 may totally manage all checkup receiver information obtained from a plurality of health checkup apparatuses 100 connected to the checkup receiver information storage apparatus 200 through the network 300.

Figure 2:
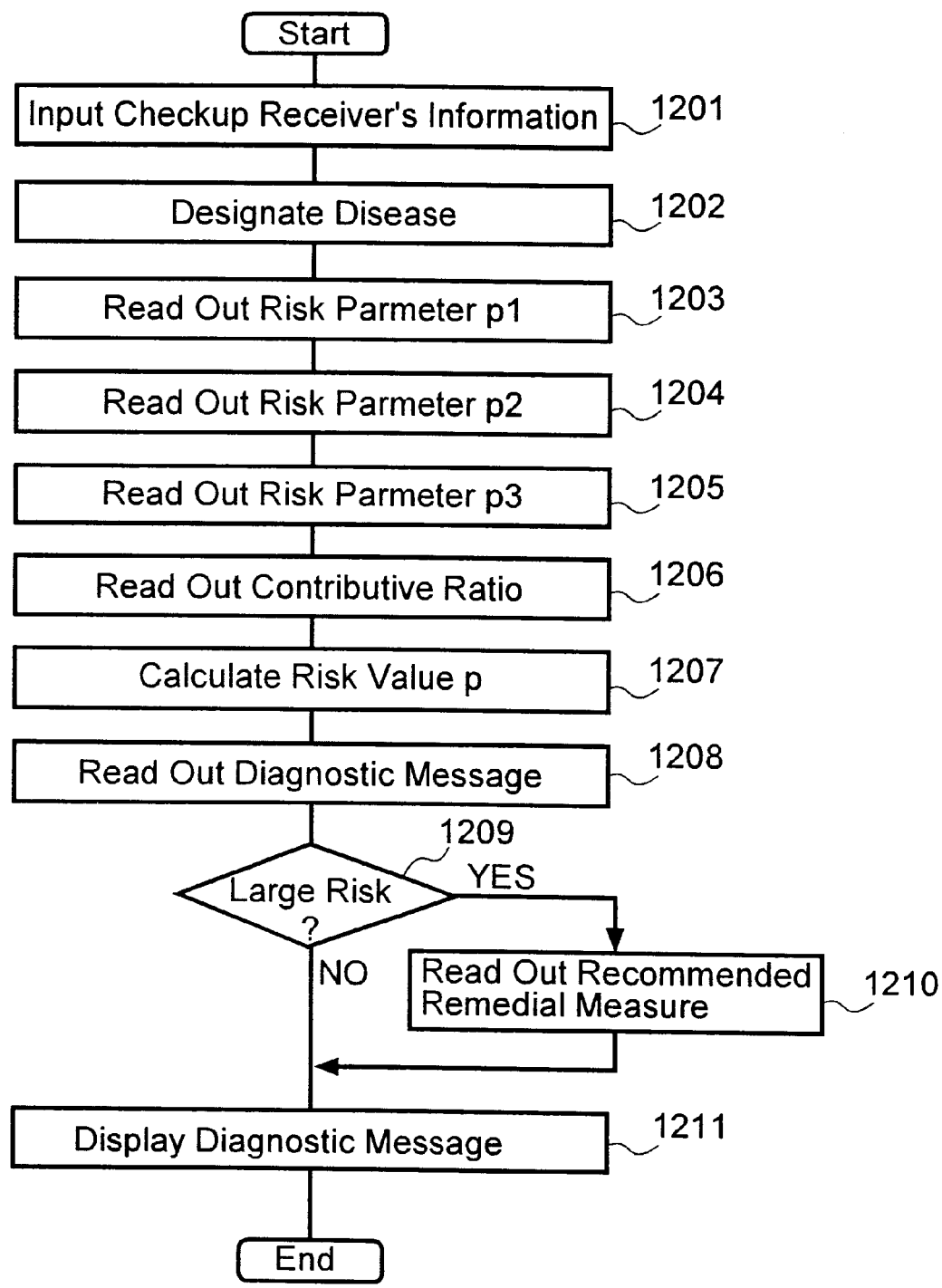
FIG. 2 is a flowchart indicting steps of risk predicting processing according to the present invention.

FIG. 2 is a flowchart showing steps of risk prediction processing according to the present invention. In Step 1201, the checkup receiver information inputting and processing section 110 of the health checkup apparatus 100 receives the results of a clinical examination, the results of a question-and-answer examination and the results of a genetic examination as checkup receiver information.

FIG. 3 is a table showing an example of a checkup receiver information according to the present invention. As shown in FIG. 3, checkup receiver information in this embodiment of the present invention includes a checkup receiver ID 301, a data entry date 302, the results of a clinical examination 303, the results of a question-and-answer examination 304 and the results of a genetic examination 305.

The checkup receiver ID 301 is an identification number to identify a specific checkup receiver. The data entry date 302 includes a year, a month and a date when the checkup receiver information was inputted. The results of a clinical examination 303 are data indicating the bio-information of the checkup receiver obtained through various examinations.

The results of a question-and-answer examination 304 are checkup receiver-related data including the daily habits and other aspects of the checkup receiver obtained through an entry of data on an interview sheet. The results of a genetic examination 305 include information indicating the genetic characteristics of a checkup receiver and show data indicating whether the genes of the checkup receiver has gene mutation associated with the incidence of any disease.

FIG. 3 shows an example of diabetes-related checkup receiver information. In the results of a clinical examination 303 according to the present invention, a fasting blood glucose value and values shown in a glucose tolerance test and glycuresis have numerical indications designating a specific range of values. For example, the fasting glucose value of the checkup receiver is in the range of a glucose value represented by numeral 1. It should be noted that, when this value is larger, an actually measured value corresponding to it as shown in the results of the corresponding clinical examination 303 is larger.

A circle in the results of a question-and-answer examination 304 indicates that the checkup receiver answered "yes" to a question "Q1," etc. on an interview sheet and a blank box in the results of the question-and-answer examination 304 indicates a "no" answer. "NIDDM1" in the results of a genetic examination 305 shows a gene associated with incidence of non-insulin dependent diabetes, with a circle indicating that the checkup receiver has its gene mutation and a blank indicating the absence of such gene mutation.

FIG. 4 is a diagram showing an example of a question-and-answer examination interview sheet according to the present invention. Shown in FIG. 4 is an interview sheet used for a diagnosis of diabetes. The daily-intake of calories and habitual activities, such as regular exercise, may be added.

Then, in Step 1202 shown in FIG. 2, the risk prediction processing section 111 accepts the designation of a disease subject to a risk prediction. In Step 1203, risk parameters p1 corresponding the results of a checkup receiver's clinical examination 303 are read from the clinical examination result parameter table 107.

FIG. 5 shows an example of the clinical examination result parameter table 107 according to the present invention. As shown in FIG. 5, the clinical examination result parameter table 107 represents the probability of suffering from diabetes within a specific period as a risk parameter p1 for checkup receivers associated with the clinical examination results. Out of checkup receivers with fasting blood glucose, a glucose tolerance test and glycuresis showing values "1", "2" and "4" respectively, 31 percent are shown to suffer from diabetes within a specific period. A fasting blood glucose value and values indicated by fasting blood glucose, a glucose tolerance test and glycuresis as shown in the clinical test result parameter table 107 have numerical indications specifying a scope of specific values for each item as shown in FIG. 3.

In Step 1204, a risk parameter p2 corresponding to the results of a question-and-answer examination 304 of a checkup receiver as shown in FIG. 3 is read from the question-and-answer examination result parameter table 108.

FIG. 6 shows an example of the question-and-answer examination result parameter table 108. The question-and-answer examination result parameter table 108 as shown in FIG. 6 represents the probability of suffering from diabetes within a specific period as a risk parameter p2 for checkup receivers associated with the question-and-answer examination results. Like FIG. 3, incidentally, a circle to a question such as Q1 in the interview sheet represents a "yes" answer to that question and a blank means "no."

In Step 1205, a risk parameter p3 corresponding to the results of a genetic examination 305 of a checkup receiver as shown in FIG. 3 is read from the genetic examination result parameter table 109.

Figure 7:
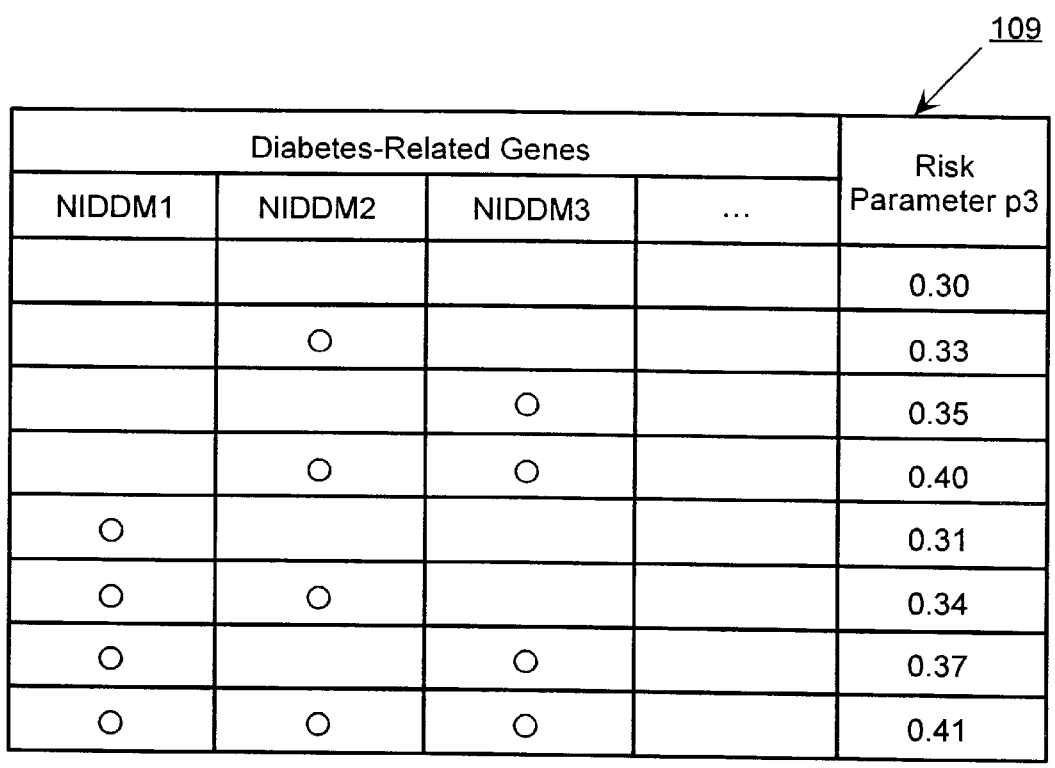
FIG. 7 is a table showing an example of a genetic examination result parameter table 109 according to the present invention.

FIG. 7 shows an example of the genetic examination result parameter table 109. As shown in FIG. 7, the genetic examination result parameter table 109 represents the probability of suffering from diabetes within a specific period as a parameter p3 for checkup receivers' associated with the genetic examination results. Like FIG. 3, each entry for a diabetes-related gene, such as "NIDDM1," shows a gene associated with the incidence of non-insulin dependent diabetes mellitus (NIDDM), with a circle indicating that a checkup receiver has a gene mutation and a blank indicating that a checkup receiver has no gene mutation.

In Step 1206, parameters each showing a contributive ratio to the risk value of each risk parameter a, b or c is read out and, in Step 1207, a risk value P is calculated through the following formula.

$$P = a \cdot p1 + b \cdot p2 + c \cdot p3 \qquad \text{(Equation 1)}$$

The equation 1 shows an example of formulas used to calculate a risk value in Step 1207. P is a risk value showing the probability of a checkup receiver suffering from a disease within a specific period; p1 is a risk parameter showing the probability of disease incidence within a specific period calculated on the basis of results of the past clinical examinations; p2 is a risk parameter showing the probability of disease incidence within a specific period calculated on the basis of results of the past question-and-answer examination; and p3 is a risk parameter showing the probability of disease incidence within a specific period calculated on the basis of results of the past genetic examinations.

Meanwhile, a is the contributive ratio of the results of a clinical examination contributing to a general risk with respect to the specific disease, b is the contributive ratio of the results of a question-and-answer examination contributing to the general risk with respect to the specific disease and c is the contributive ratio of the results of a genetic examination contributing to the general risk with respect to the specific disease, their relationship being shown as a+b+c=1.

In Step 1208, a diagnostic message corresponding to the risk value P calculated as described above is read out. In Step 1209, it is verified whether or not the above calculated risk value P is higher than a predetermined level and, if it is, remedial measures are read out from the recommended remedial measure presenting processing section 112 in Step 1210.

In Step 1211, a diagnostic message corresponding to the risk value P calculated as described above is displayed and remedial measures are presented if they are read out in Step 1210.

For example, when the calculated risk value P is low, a message like "Your probability of the incidence of diabetes is less than P%. You don't need to pay any special attention in your daily life." is displayed.

When the calculated risk value P is high, a diagnostic message like "Your values of diabetes-related items subject to the clinical examination are high and, judged together with genetic factors, your probability of the incidence of diabetes is P%. You need to change your habitual activities and it is recommended that you receive a detailed health checkup every six months." is displayed. As remedial measures the recommended remedial measure processing section 112, after its processing, displays a daily total calorie intake, urging a calorie intake limitation and aerobics exercise to consume fat, in Step 1210.

These diagnostic messages and remedial measures are set beforehand for applicable risk values P and values of items applicable to checkup receiver information.

As described above, in addition to the results of a clinical examination 303 indicating the bio-information of the checkup receiver and the results of a question-and-answer examination 304 including information showing the habitual activities, etc. of a checkup receiver, the embodiment of the present invention uses the results of a genetic examination 305 indicting the genetic characteristics of the checkup receiver for a diagnosis, so that it is possible to diagnose a checkup receiver's risk of contracting a life-dependent disease, etc. based on habitual activities and genetic characteristics, making such a diagnosis match the characteristics of the checkup receiver.

Since a diagnosis is conducted on the basis of environmental factors such as habitual activities and the results of a genetic examination combined in this embodiment of the present invention, it is possible to diagnose a disease which could not be diagnosed only through a genetic examination and to widen a scope of diagnosable diseases.

After the above diagnostic messages and recommended remedial measures are displayed, the risk predicting processing section 111 completes its processing by sending the inputted check receiver information to the checkup receiver information storage apparatus 200. The checkup receiver information storage and processing section 210 of the checkup receiver information storage apparatus 200 stores in the checkup receiver information database 207 the checkup receiver information at the time of a health checkup or a patient's information at the time of disease incidence transmitted as explained above.

FIG. 8 is a table showing an example of the checkup receiver information database 207 according to the present invention. As shown in FIG. 8, the checkup receiver information database 207 according to the present invention includes a checkup receiver ID 801, the date of a data entry 802, the results of a clinical examination 803, the results of a question-and-answer examination 804, the results of a genetic examination 805 and a history of diseases 806.

The checkup receiver ID 801 is an identification number to identify a checkup receiver. The date of a data entry 802 includes a year, a month and a date when the checkup receiver information was inputted. The results of a clinical examination 803 are data showing the bio-information of the checkup receiver obtained through various examinations.

The results of a question-and-answer examination 804 are the checkup receiver-related data, including information on the habitual activities, etc. of the checkup receiver obtained through an entry an interview sheet. The results of a genetic examination 805 including information indicating the genetic characteristics of the checkup receiver are data on the genes of the checkup receiver diseases-causing gene mutation. The history of diseases 806 lists up the names of diseases the checkup receiver has suffered from in the past.

As shown in FIG. 8, the checkup receiver information database 207 stores the history of diseases 806 of a checkup receiver together with the checkup receiver information as shown in FIG. 3. The information accumulated in the checkup receiver information database 207 is used for the calculation of the above-described risk Parameters and their contributing ratios.

Figure 9:
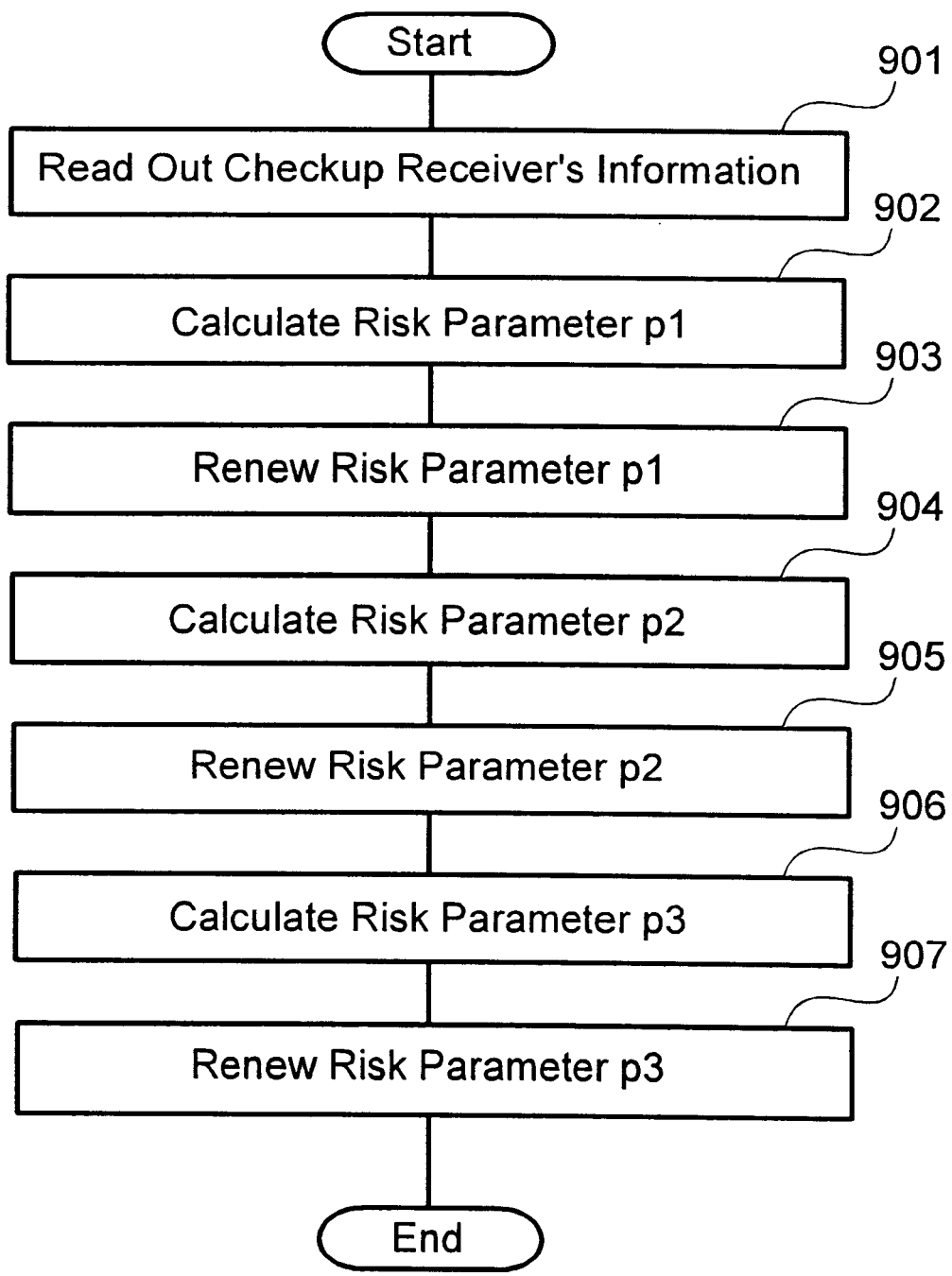
FIG. 9 is a flowchart showing steps of risk parameter calculation processing according to the present invention.

FIG. 9 is a flowchart showing steps of risk parameter calculation processing. The risk parameter calculation processing section 211 of the checkup receiver information storage apparatus 200 starts its operation when specific conditions are satisfied, such as when the checkup receiver information database 207 is renewed or a predetermined period elapses from the previous calculation processing. In Step 901, it reads out from the checkup receiver information database 207 the checkup receiver information over a predetermined period.

In Step 902, checkup receivers corresponding to each other in the clinical examination 803 out of the above read-out checkup receiver information are counted, with reference to the history of diseases 806 out of the checkup, receiver information the ratio of checkup receivers, suffering from a specific disease among the checkup receivers is calculated every disease, and a risk parameter p1 for each disease is found.

In Step 903, the risk parameter p1 obtained as described above is sent to the health checkup apparatus 100. The health checkup apparatus 100 stores the received risk parameter p1 in the clinical examination result parameter table 107.

In Step 904, checkup receivers corresponding to each other in the question-and-answer examination 804 out of the above read-out checkup receiver information are counted, with reference to the history of diseases 806 out of the checkup receiver information the ratio of checkup receivers' suffering from a specific disease among the checkup receivers is calculated for every disease, and a risk parameter p2 for each disease is found.

In Step 905, the risk parameter p2 worked out as described above is sent to the health checkup apparatus 100. The health checkup apparatus 100 stores the received risk parameter p2 into the question-and-answer result parameter table 108.

In Step 906, checkup receivers corresponding to each other in the genetic examination results 805 out of the above read-out checkup receiver information are counted and, with reference to the history of diseases 806, the ratio of checkup receiver's suffering from a specific disease among the checkup receivers is calculated for every disease and a risk parameter p3 for each disease is found.

In step 907, the risk parameter p3 worked out as described above is sent to the health checkup apparatus 100. The health checkup apparatus 100 stores the received risk parameter p3 in the genetic examination result parameter table 109.

Figure 10:
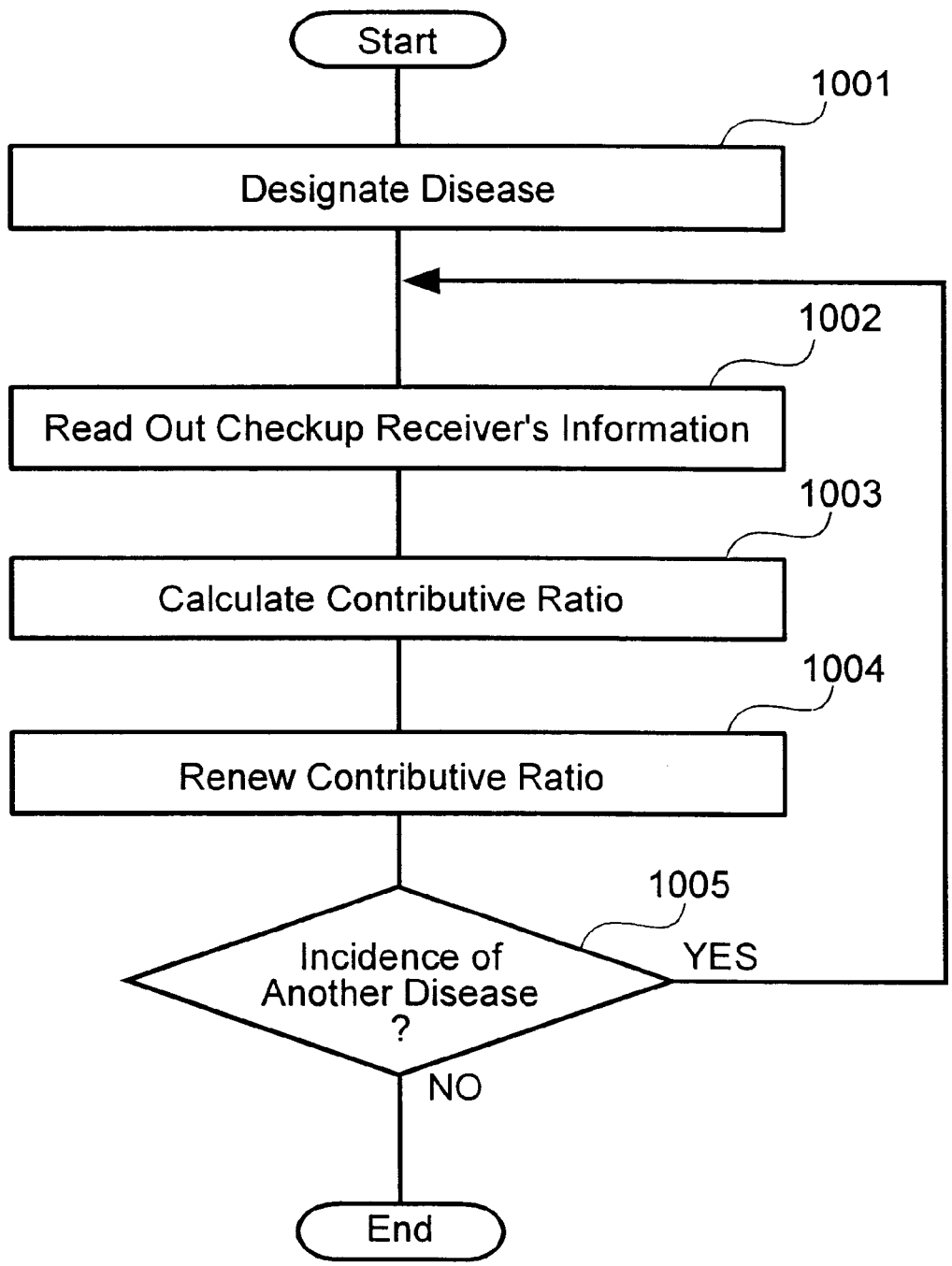
FIG. 10 is a flowchart showing steps of contributive ratio calculation processing according to the present invention.

FIG. 10 is a flowchart showing steps of the contributive ratio calculation processing according to the present invention. Like the risk parameter calculation processing section 211, the contributive ratio calculation processing section 212 of the checkup receiver information storage apparatus 200 starts its operation when specific conditions are satisfied, such as when the checkup receiver information database 207 is renewed or a predetermined period elapses from the previous calculation processing. In Step 1001, a disease to calculate its contributive ratio first is selected and set out of the history of disease 806 in the checkup receiver information database 207.

The checkup receiver information of the checkup receiver's suffering from the designated disease is read out from the checkup receiver information database 207 in Step 1002, relationships between the results of a clinical examination 803, the results of a question-and-answer examination 804 and the results of a genetic examination 805 for the read-out checkup receiver information and, the designated disease are studied, and contributive ratios a, b and c weighted in accordance with the strength of their relationships are calculated.

With dispersions obtained for objective items of the results of a clinical examination 803, the results of a question-and-answer examination 804 and the results of a genetic examination 805 for the read-out checkup receiver information, for example, a, b and c as contributive ratios in proportion to their reciprocals are calculated. In this embodiment of the present invention, a contributive ratio is calculated for each item of the results of a clinical examination 603, the results of a question-and-answer examination 804 and the results of a genetic examination 805. In a case where objective items for such contributive ratio calculation processing are diversified and a number of items not specifically relating to the incidence of the designated disease are included, a contributive ratio for each item is used to calculate the risk value P by utilizing a contributive ratio calculated for each objective item.

In Step 1004, the contributive ratio obtained as described above is sent to the health checkup apparatus 100. The health checkup apparatus 100 stores the received contributive ratio as the contributive ratios a, b and c to calculate the risk value P of the disease.

In Step 1005, a disease is searched for in the history of disease 806 of the checkup receiver information database 207. It is also checked to see whether there is a disease for which a contributive ratio has not been calculated and, if there is, the processing returns to Step 1002 with the name of that disease designated. When contributive ratios are calculated for all the diseases stored in the history of diseases 806 of the checkup receiver information database 207, this processing is completed and finished.

As described above, this embodiment of the present invention sends checkup receiver information inputted from the health checkup apparatus 100 to the checkup receiver information storage apparatus 200 to calculate risk parameters and their contributive ratios at the checkup receiver information storage apparatus 200 and to feed them back to the health checkup apparatus 100, so that it is possible to heighten the precise calculation of risk values as checkup receiver information is accumulated.

According to the health checkup system embodying the present invention as described above, the prediction of a check receiver's risk liability to a disease is conducted with the results of a genetic examination indicating the genetic characteristics of an individual added to the results of a clinical system and the results of a question-and-answer examination, making it possible to enhance the precision of the calculation of a checkup receiver's disease-incidence risk value.

According to the present invention, the health checkup system conducts a risk prediction of a disease of a checkup receiver based on the results of a genetic examination indicating the genetic characteristics of an individual together with the results of a clinical examination and a question-and-answer examination, so that the precision of the calculation of a risk value with respect to a health checkup receiver can be enhanced.

What is claimed is:

1. A health checkup supporting method for predicting a checkup receiver's risk of suffering from a disease, said method comprising the steps of:

inputting checkup receiver information indicating information showing the possibility of affecting the incidence of a disease obtained with respect to a checkup receiver who has received a health checkup; and finding a value of a risk of the checkup receiver's suffering from the disease based on said inputted checkup receiver information and risk parameters obtained from a ratio of the past checkup receivers' suffering from the disease;

wherein said checkup receiver information includes results of a clinical examination, results of a question-and-answer examination, and results of a genetic examination conducted with respect to the checkup receiver.

2. A health checkup supporting method as defined in claim 1, further comprising a step of presenting remedial measures recommended to lower the risk value when said risk value is higher than a predetermined level.

3. A health checkup supporting method as defined in claim 2, wherein the results of the clinical examination are results of a physical testing of the checkup receiver, and the results of the genetic examination are results of a gene based testing of the checkup receiver.

4. A health checkup supporting method as defined in claim 1, wherein the finding of the value of a risk of the checkup receiver's suffering from the disease is at least one of a determined percentage value and a relationship with respect to a percentage value.

5. A health checkup supporting apparatus for predicting a checkup receiver's risk of suffering from a disease, said apparatus comprising:

a checkup receiver information inputting and processing section for inputting checkup receiver information indicating information showing the possibility of affecting the incidence of a disease obtained with respect to a checkup receiver who has received a health checkup; and a risk prediction calculation section for finding a value of a risk of the checkup receiver's suffering from the disease based on said inputted checkup receiver information and risk parameters obtained from a ratio of the past checkup receivers' suffering from the disease;

wherein said checkup receiver information includes results of a clinical examination, results of a question-and-answer examination, and results of a genetic examination conducted with respect to the checkup receiver.

6. A health checkup supporting apparatus as defined in claim 5, further comprising a remedial measures presenting and processing section for presenting remedial measures recommended to lower the risk value when said risk value is higher than a predetermined level.

7. A health checkup supporting apparatus as defined in claim 5, wherein the results of the clinical examination are results of a physical testing of the checkup receiver and the results of the genetic examination are results of a gene based testing of the checkup receiver.

8. A health checkup supporting as defined in claim 5, wherein said risk prediction calculation section determines the value of the risk of the checkup receiver's suffering from the disease in terms of is at least one of a determined percentage value and a relationship with respect to a percentage value.

9. A computer readable recording medium storing a program enabling a computer to function as a health checkup apparatus for predicting a checkup receiver's risk of suffering from a disease, said computer comprising:

a checkup receiver information inputting and processing section for inputting checkup receiver information indicating information showing the possibility of affecting the incidence of a disease obtained with respect to a checkup receiver who has received a health checkup; and a risk prediction processing section for finding a value of a risk of the checkup receiver's suffering from a disease based on said inputted checkup receiver information and risk parameters obtained from a ratio of the past checkup receivers' suffering from the disease;

wherein said checkup receiver information includes results of a clinical examination, results of a question-and-answer examination, and results of a genetic examination conducted with respect to the checkup receiver.

10. A recording medium as defined in claim 9, further comprising a remedial measures presenting and processing section for presenting remedial measures recommended to lower the risk value when said risk value is higher than a predetermined level.

11. A computer readable recording mediums defined in claim 9, wherein the results of the clinical examination are results of a physical testing of the checkup receiver and the results of the genetic examination are results of a gene based testing of the checkup receiver.

12. A computer recording medium as defined in claim 9, wherein said risk prediction processing section finds the value of the risk of the checkup receiver's suffering from a disease in terms of at least one of a determined percentage value and a relationship with respect to a percentage value.

13. A health checkup supporting method for predicting a checkup receiver's risk of suffering from a disease, said method comprising the steps of:

inputting checkup receiver information of a receiver who has received a health checkup including results of a clinical examination of the checkup receiver, results of genetic examination of the checkup receiver, and results of information obtained through a question-and-answer examination of the checkup receiver;

finding a value of a risk of the checkup receiver's suffering from the disease by finding relationship between the checkup receiver information and a ratio of suffering from the disease based on said inputted checkup receiver information and information obtained from the ratio of the past checkup receivers' suffering from the disease.

14. A health checkup supporting method as defined in claim 13, comprising, in a step of finding the value of a risk of the checkup receiver's suffering from the disease by finding relationship between the checkup receiver information and the ratio of suffering from the disease, a step of finding relationship between the incidence of the disease and each of results of a clinical examination, genetic information and the checkup receiver information obtained through a question-and-answer examination and weighting the respective relationships to calculate the value of a risk of the checkup receiver's suffering from the disease.

15. A health checkup supporting method as defined in claim 13, wherein the results of the clinical examination are results of a physical testing of the checkup receiver and the results of the genetic examination are results of a gene based testing of the checkup receiver.

16. A health checkup supporting method as defined in claim 13, wherein the finding of the value of a risk of the checkup receiver's suffering from the disease is at least one of a determined percentage value and a relationship with respect to a percentage value.

* * * * *